United States Patent
Caby et al.

(10) Patent No.: US 7,162,306 B2
(45) Date of Patent: Jan. 9, 2007

(54) INTERNAL MEDICAL DEVICE COMMUNICATION BUS

(75) Inventors: Glen D. Caby, Lake Forest Park, WA (US); James S. Neumiller, Redmond, WA (US); Jyhlin Chang, Shoreline, WA (US); Curtis R. Jordan, Kent, WA (US); Dana J. Olson, Kirkland, WA (US); Ward A. Silver, Vashon, WA (US); Scott O. Schweizer, Snohomish, WA (US)

(73) Assignee: MedTronic Physio - Control Corp., Redmond, WA (US)

( * ) Notice: Subject to any disclaimer, the term of this patent is extended or adjusted under 35 U.S.C. 154(b) by 531 days.

(21) Appl. No.: 09/992,708

(22) Filed: Nov. 19, 2001

(65) Prior Publication Data

US 2003/0097160 A1    May 22, 2003

(51) Int. Cl.
*A61N 1/39*    (2006.01)
(52) U.S. Cl. ............................................ 607/60; 607/5
(58) Field of Classification Search .................... None
See application file for complete search history.

(56) References Cited

U.S. PATENT DOCUMENTS

| | | | | |
|---|---|---|---|---|
| 5,734,373 A | * | 3/1998 | Rosenberg et al. | 345/161 |
| 5,987,519 A | | 11/1999 | Peifer et al. | |
| 6,148,233 A | * | 11/2000 | Owen et al. | 607/5 |
| 6,415,343 B1 | * | 7/2002 | Fensore et al. | 710/104 |
| 6,547,730 B1 | * | 4/2003 | Lin et al. | 600/437 |
| 6,826,639 B1 | * | 11/2004 | Pasumansky et al. | 710/105 |
| 6,832,200 B1 | * | 12/2004 | Greeven et al. | 705/3 |
| 2003/0035473 A1 | * | 2/2003 | Takinosawa | 375/224 |

* cited by examiner

*Primary Examiner*—Robert E. Pezzuto
*Assistant Examiner*—Kristen Mullen
(74) *Attorney, Agent, or Firm*—Shumaker & Sieffert

(57) ABSTRACT

In general, the invention facilitates improved inter-module communication within a medical device system, such as an automated external defibrillator (AED), by using a serial data interface based on the USB specification to transfer data between modules. As a result, data transmission rates may be improved significantly, thereby providing ample communication bandwidth for a variety of medical device applications. Further, the serial interconnect nature of the USB interface reduces the number of physical interconnects that are needed to support the interface, thereby reducing the design constraints on the medical device system.

34 Claims, 3 Drawing Sheets

INTERNAL MEDICAL DEVICE COMMUNICATION BUS

TECHNICAL FIELD

The invention relates generally to medical devices and, more specifically, to communication between modular components of a medical device.

BACKGROUND

Ventricular fibrillation and atrial fibrillation are common and dangerous medical conditions that cause the electrical activity of the human heart to become unsynchronized. Loss of synchronization may impair the natural ability of the heart to contract and pump blood throughout the body. Medical personnel treat fibrillation by using a defibrillator system to apply a relatively large electrical charge to the heart. If successful, the charge overcomes the unsynchronized electrical activity and gives the natural pacing function of the heart an opportunity to recapture and reestablish a normal sinus rhythm.

Defibrillator systems are medical instruments that may have multiple components, including, for example, a defibrillator to apply an electrical shock to the heart of a patient, and an electrocardiogram (ECG) monitor to evaluate the condition of the patient. More particularly, the monitor records and analyzes an ECG signal from the patient, while the defibrillator produces a high-energy defibrillation pulse to terminate ventricular or atrial fibrillation.

One or more of these components may incorporate several modules. The defibrillator, for example, may include modules for obtaining information from the patient, interacting with the operator of the defibrillator, and delivering therapy to the patient. This modular approach facilitates customization of the defibrillator to the needs of the particular application. For example, a user interface module may be selected based on the level of experience of the expected operator of the defibrillator.

The defibrillator modules typically communicate with each other using a serial data connection. In some conventional defibrillators, inter-module communication occurs over an RS-232 connection. Other conventional defibrillators use various types of serial data connections, including, for example, I²C, Microwire, or SPI connections. These types of connections have a number of disadvantages. For example, the bandwidth realized by these connections may be too low for certain applications. In addition, these connections lack extensibility. That is, flexibility in allocating functionality among various modules is limited.

SUMMARY

In general, the invention facilitates improved inter-module communication within a medical device system, such as an automated external defibrillator (AED), by using a serial data interface based on the USB specification to transfer data between modules. USB-type interfaces have conventionally been used to connect devices externally, e.g., to connect various types of peripheral devices to a personal computer. According to the principles of the invention, however, a USB-type interface connects devices or modules internally within a medical device system. This interface transfers data using the USB data communication protocol and complies with USB specifications with respect to signal integrity and impedances, but employs a physical connector module designed for the space-limited environment within a medical device system.

The invention may offer several advantages. For instance, data transmission rates may be improved significantly, thereby providing ample communication bandwidth for a variety of medical device applications. Further, the serial interconnect nature of the USB interface reduces the number of physical interconnects that are needed to support the interface, thereby reducing the design constraints on the medical device system. Costs associated with manufacturing the medical device system may also be reduced.

One embodiment is directed to a method for transferring data between modules of a medical device using a USB protocol. A USB token packet is transmitted to a first module of a medical device system. When the first module has a USB data packet to transfer, the data packet is received from the first module. The data packet is transferred to a second module of the medical device system. Modules of the medical device may be programmed or upgraded in this manner.

Other implementations include defibrillators that carry out these methods, as well as processor-readable media containing instructions that cause a processor within a medical device to perform these methods. For example, in one embodiment, a medical device includes a system control module, functional modules, and a system bus coupled to the system control module and to the plurality of functional modules. The system bus transfers data packets between the functional modules and the system control module according to the USB protocol. The functional modules may include, for example, a therapy control module that controls a therapy device, such as a set of defibrillator electrodes, a user interface module, and a patient parameters module.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
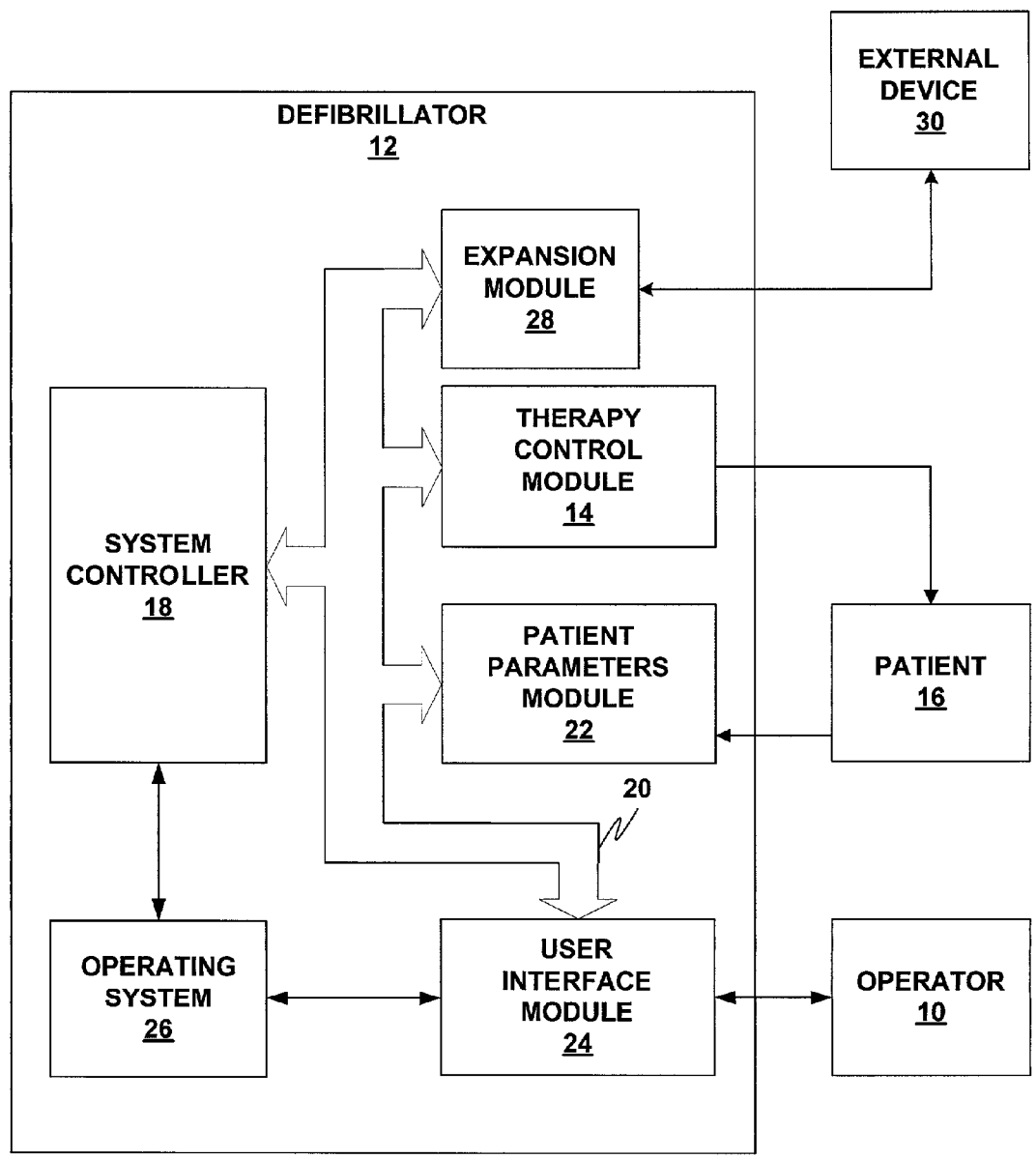
FIG. 1 is a block diagram illustrating a defibrillating system configured according to an embodiment of the invention.

FIG. 1 is a block diagram illustrating a defibrillating system in which the invention may be practiced. When activated by an operator 10, a defibrillator 12 administers one or more electric shocks via defibrillator electrodes to a patient 16. Defibrillator 12 may be implemented, for example, as an automated external defibrillator (AED).

Operation of defibrillator 12 is controlled by a system controller 18 that is connected to a system bus 20. System controller 18 may be implemented as a microprocessor that communicates control and data signals with other components of defibrillator 12 using the USB protocol via system bus 20. These components may include functional modules, such as therapy control module 14 or other therapy control modules, a patient parameters module 22, and a user interface module 24.

Therapy control module 14 causes defibrillator electrodes (not shown) to deliver electric shocks to patient 16 in response to control signals received from system controller 18 via system bus 20. Therapy control module 14 may include, for example, charging circuitry, a battery, and a discharge circuit. Any or all of these components can be controlled by system controller 18.

Patient parameters module 22 may include electrocardiogram (ECG) leads or other inputs. Patient parameters module 22 collects information from patient 16, including, for example, vital signs, non-invasive blood pressure (NIBP) measurements, and $SpO_2$ information. Other information relating to patient 16 may be collected by patient parameters module 22, including, but not limited to, EEG measurements, invasive blood pressure measurements, temperature measurements, and $ETCO_2$ information.

User interface module 24 receives input from operator 10 and outputs information to operator 10 using any of a variety of input and output devices. For example, operator 10 may use keys to input commands to defibrillator 12 and receive prompts or other information via a display screen or LED indicators. As an alternative, the display screen may be implemented as a touch-screen display for both input and output. In addition, user interface module 24 may print text reports or waveforms using a strip chart recorder or similar device. User interface module 24 may also interface with a rotary encoder device.

User interface module 24 provides input received from operator 10 to an operating system 26 that controls operation of defibrillator 12 via system controller 18. Operating system 26 may be implemented as a set of processor-readable instructions that are executed by system controller 18. When defibrillator 12 is activated, operating system 26 causes therapy control module 14 to deliver therapeutic shocks to patient 16 via defibrillator electrodes according to an energy protocol.

As described above, system controller 18, therapy control module 14, patient parameters module 22, and user interface module 24 are connected to each other via system bus 20. According to an embodiment of the invention, system bus 20 is compatible with the USB standard. Implementing system bus 20 as a USB-compatible bus offers several benefits. Advantageously, these modules may communicate with each other using significantly fewer interconnects compared to other communication schemes. For example, one conventional interconnect technique uses a peripheral component interconnect (PCI) bus that, in some implementations, uses more than one hundred interconnects. As a result, systems using a PCI bus must satisfy strict design constraints, such as size and power constraints. By contrast, USB-compatible system bus 20 may use only four interconnects, facilitating implementation within significantly fewer design constraints. Moreover, the USB communication protocol is simple, reducing the complexity of the logic required in USB support chips. The reduced constraints and simple communication protocol lead to lower costs of production, as well as improved reliability.

For purposes of inter-module communication, system controller 18, therapy control module 14, patient parameters module 22, and user interface module 24 may be considered USB devices. System controller 18 acts as a host controller that initiates all data transfers between the other modules. In addition to system controller 18, therapy control module 14, patient parameters module 22, and user interface module 24, other modules or devices can also be connected to system bus 20. For example, an expansion module 28 may allow system controller 18 to control a device 30 external to defibrillator 12. External device 30 may be a USB root hub or a USB hub connected to other devices, such as data acquisition devices or other USB-compatible devices. Using a USB hub, many devices can be connected to defibrillator 12 for a variety of purposes. Some such devices include, but are not limited to, a printer, a bar code scanner, a computer keyboard, or a data transfer device. These devices may either be simple devices or complex devices as defined in the USB specification.

Figure 2:
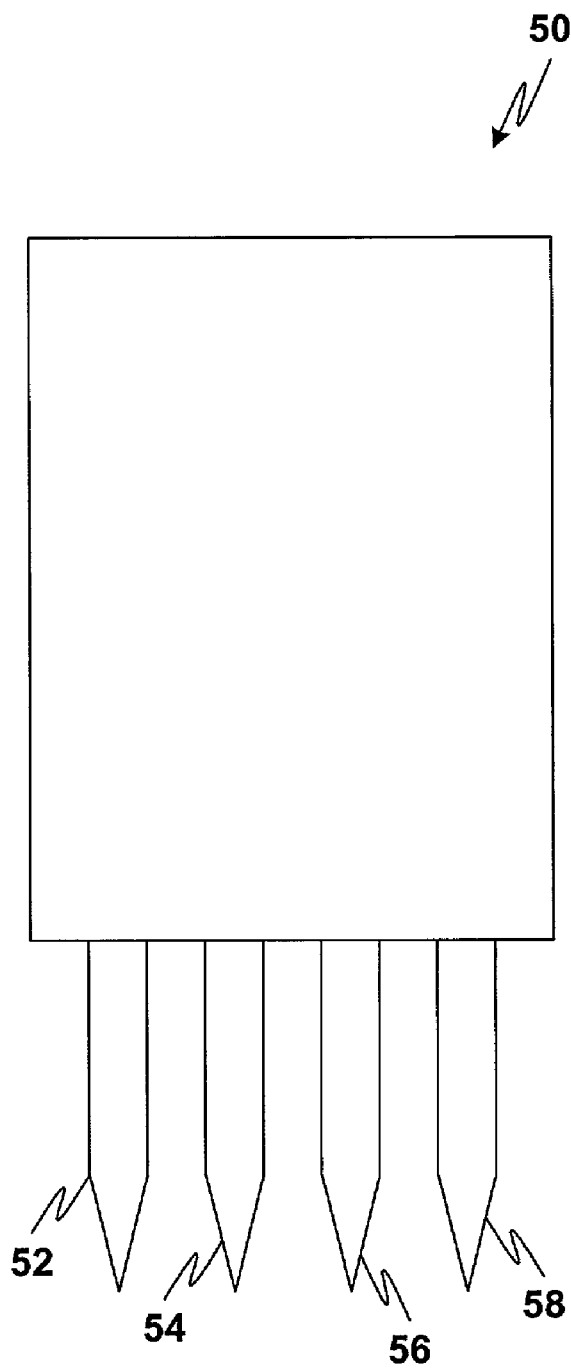
FIG. 2 is a plan view of a connector module for connecting a device or module to the system controller of FIG. 1.

FIG. 2 is a plan view of a connector module 50 for connecting a device or module to system controller 18. Connector module 50 includes a number of pins 52, 54, 56, and 58 that may be inserted into appropriate receptacles in devices or modules to transfer ground and data signals. For example, in one embodiment, pins 52 and 54 may be used for ground, while pins 56 and 58 may be used to transfer data signals. The allocation of ground and data lines among pins 52, 54, 56, and 58 may be selected to satisfy impedance requirements. Allocating two pins to ground connections allows greater flexibility in impedance matching, potentially improving signal integrity. As an alternative, a single pin may be allocated to ground, such that connector module 50 may include only three pins, rather than four as shown. In addition, one or more of system controller 18, therapy control module 14, patient parameters module 22, and user interface module 24 may incorporate impedance matching circuitry to satisfy the impedance requirements of the USB standard, thereby meeting USB signal integrity requirements.

Connector module 50 may be used to connect any of the devices or modules internal to defibrillator 12, e.g., system controller 18, a therapy control module 14, patient parameters module 22, user interface module 24, and expansion module 28, to system bus 20. Expansion module 28 has a USB port for connecting an external USB-compatible device to system bus 20 via a conventional flex circuit cable that meets USB specifications for impedance and signal integrity. The flex cable allows expansion module 28 to reside within defibrillator 12 at some distance, e.g., approximately 2–12 inches (5–30 cm) away from system controller 18. In addition to carrying the USB-standard signals, the flex cable may also carry several additional signals that do not relate to USB communication. While not required, the flex cable may also be used to connect other devices or modules internal to defibrillator 12, such as user interface module 24. External devices 30 may be connected to expansion module 28 via a conventional USB cable.

While the physical interface between the various devices or modules and system bus 20 differs from the USB standard, communication between the devices conforms to the USB communication protocol, as well as USB specifications relating to impedance and signal integrity. Accordingly, conventional software and hardware development tools designed for the USB standard can be used with little, if any, modification to develop additional devices for use in conjunction with defibrillator 12. Development costs are thereby reduced.

Software for transferring data between devices or modules of defibrillator 12 may incorporate conventional USB software with slight modifications. For example, the lower levels of the communication stack may be modified to support the particular processor and system controller 18 used in defibrillator 12. The software may be implemented as a set of computer-executable instructions stored in some form of computer readable media. Computer readable media can be any available media that can be accessed by defibrillator 12. By way of example, and not limitation, computer readable media may comprise computer storage media and communication media. Computer storage media includes volatile and nonvolatile, removable and nonremovable media implemented in any method or technology for storage of information, such as computer readable instructions, data structures, program modules, or other data. Computer storage media includes, but is not limited to, random access memory (RAM), read only memory (ROM), EEPROM, flash memory or other memory technology, CD-ROM, digital versatile discs (DVD) or other optical storage, magnetic cassettes, magnetic tape, magnetic disk storage or other magnetic storage devices, or any other medium that can be used to store the desired information and that can be accessed by defibrillator 12. Communication media typically embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or other direct-wired connection, and wireless media, such as acoustic, RF, infrared, and other wireless media. Combinations of any of the above computer storage media and communication media are also included within the scope of computer-readable media.

Figure 3:
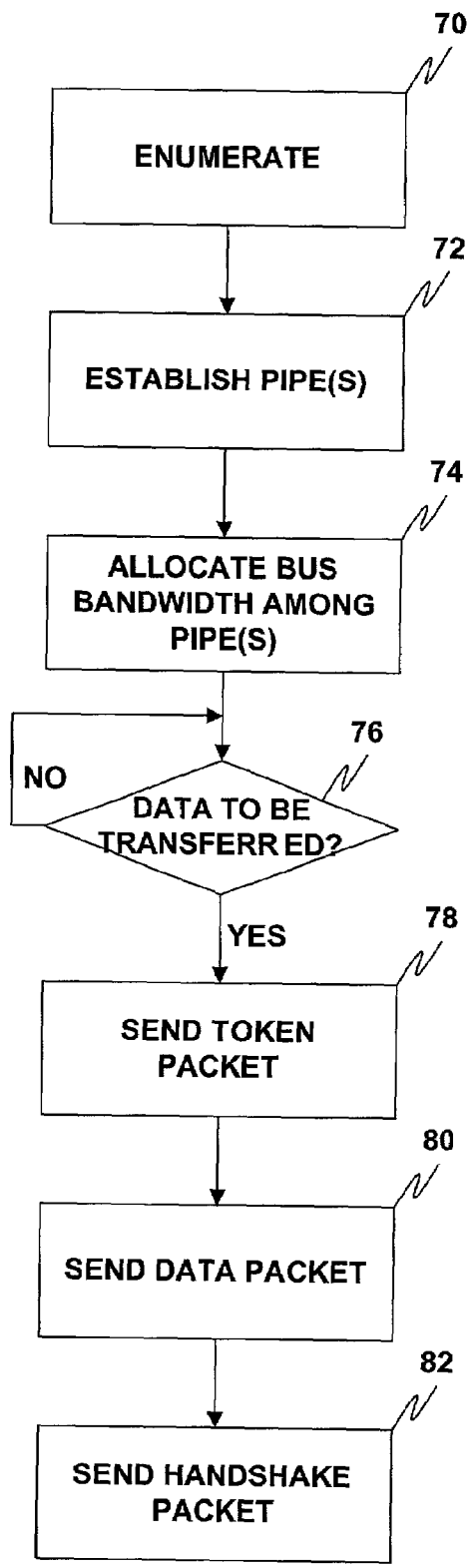
FIG. 3 is a flow diagram illustrating an example mode of operation of the defibrillator system of FIG. 1.

FIG. 3 is a flow diagram illustrating an example mode of operation that may be implemented by the USB software. Before any data is transferred, system controller 18 assigns USB addresses to devices or modules as they are connected to system bus 20 during a process known as enumeration (70). These addresses are subsequently used to address individual devices. In addition, when a device is connected to system bus, associations between system controller 18 and one or more endpoints of the device are established (72). These associations are known as pipes. A given device may have multiple pipes. For example, user interface module 24 may have an endpoint that supports a pipe for transferring data to user interface module 24 and another endpoint that supports another pipe for transferring data from user interface module 24. When multiple pipes are established, the available bandwidth of system bus 20 is allocated among the pipes (74). For some pipes, bandwidth is allocated when the pipe is established.

All devices must support a specially designated control pipe. All devices support a common access mechanism for accessing information through the control pipe. For example, system controller 18 can access device information via the control pipe. This device information may be categorized as standard information whose definition is common to all devices, as class information specific to the type or class of the device, or as vendor-specific information. In addition to device information, system controller 18 may access USB control and status information via the control pipe.

Other pipes may be used to transfer functional data and control information between system controller 18 and other devices via system bus 20. Such pipes may be either uni-directional or bi-directional. Generally, data movement through one pipe is independent from data movement in other pipes.

System bus 20 is a polled bus. That is, system controller 18 periodically polls (76) the devices connected to system bus 20 to determine whether a device has data to be transferred to system controller 18 or to another device connected to system bus 20. If there is no data to be transferred, system controller 18 repeats polling the devices (76) until a device indicates that it has data to transfer.

When a device indicates that it has data to transfer, system controller 18 begins a transaction to transfer the data. Data transfers may involve the transmission of up to three packets. Each transaction begins when system controller 18 sends a USB packet, known as a token packet (78), describing the type and direction of transmission, an address designating a device or module, and an endpoint number that designates a specific endpoint associated with the device. The device or module designated by the address selects itself by decoding the appropriate address fields. In a given transaction, data is transferred either from system controller 18 to the selected device or from the selected device to system controller 18. The token packet specifies the direction of data transfer. The source of the transaction then either sends a data packet (80) or indicates that the source has no data to transfer. The destination may then respond with a handshake packet that indicates whether the transfer was successful (82).

System bus 20 may transfer data in a number of different modes. Control data, for example, is transferred in a control mode to configure a device when it is initially connected to system bus 20. Another transfer mode, known as a bulk data transfer mode, is used to transfer data that is generated or consumed in relatively large and bursty quantities, e.g., data transferred to a strip chart recorder. Bulk data is sequential. Reliable exchange of data is ensured at the hardware level by using error detection and correction techniques. The bandwidth taken up by bulk data may depend on other data transfer activities occurring on system bus 20.

Some devices or modules that send relatively small amounts of data may transfer data in an interrupt mode. In the interrupt mode, data may be presented for transfer to or from a device at any time and is delivered by system bus 20 at a rate no slower than is specified by the device. Interrupt data typically consists of event notifications or characters that are organized as one or more bytes. One example of interrupt data is characters input via the keys connected to user interface module 24.

Other devices or modules may transfer data in an isochronous mode. Isochronous data is continuous and real-time in creation, delivery, and consumption. To the extent that patient parameters module 22 collects real-time vital sign measurements from patient 16, for example, patient parameters module 22 may transfer data in the isochronous mode. In this mode, data streams between the device and system controller 18 in real-time without error correction. Timing-related information does not need to be explicitly transferred, as this information is implied by the steady rate at which the isochronous data is received and transferred. To maintain correct timing, isochronous data must be delivered at the same rate at which it is received. Accordingly, isochronous data is sensitive to the delivery rate. In addition, isochronous data may also be sensitive to delivery delays. For isochronous pipes, the bandwidth required may be based on the sampling characteristics of the associated function. The latency required may be related to the buffering available at each endpoint of the pipe.

Regardless of the data transfer mode, data transferred via system bus 20 may be encoded using a conventional inverted non return to zero (NRZI) encoding scheme. In this scheme, a value of "0" is indicated by a transition in the data signal, while a value of "1" is indicated by the absence of a transition in the data signal. Thus, for example, a string of 1's would result in a long period without signal transitions. In order to force transitions in the data signal, a bit stuffing technique is used to insert a zero after a sequence of consecutive 1's of a prescribed length, e.g., after a sequence of six consecutive 1's. Accordingly, if a device receives a sequence of consecutive 1's that exceeds the prescribed length, the device may conclude that an error has occurred and ignore the data packet.

By way of example, the data transfer technique of FIG. 3 may be used to reprogram a processor embedded in system controller 18, therapy control module 14, patient parameters module 22, or user interface module 24. Program data, such as a software upgrade, may be transferred via system bus 20 to the device to be reprogrammed. The software upgrade may then be stored using, for example, a RAM device or a flash memory.

The data transfer technique of FIG. 3 can also be used to control the functions of the various modules of defibrillator 12. For example, system bus 20 can be used to effect the delivery of therapeutic shocks to patient 16 via defibrillator electrodes. In this mode of operation, operator 10 uses the external keys to activate defibrillator 12. Operator 10 may use the external keys, for example, to select an energy protocol to be applied to patient 16. User interface module 24 transfers the key input to system controller 18 via system bus 20.

System controller 18 then generates the appropriate control signals for controlling the defibrillator electrodes to deliver the electric shock or shocks to patient 16 as specified by the selected energy protocol. System controller 18 transfers the control signals to therapy control module 14. These control signals may include control signals for controlling the charging circuitry, the discharge circuitry, or both. Therapy control module 14 operates the charging and discharge circuitry as directed by the control signals, thereby causing the defibrillator electrodes to deliver the correct electric shock or shocks to patient 16.

Various embodiments of the invention have been described. The invention may be used in AEDs as well as other types of defibrillators. In addition, while several embodiments of the invention have been described in the context of a defibrillator, the principles of the invention may be practiced in other types of medical devices, including, but not limited to, defibrillator/pacemakers and therapy devices for other medical conditions, such as stroke and respiratory conditions. These and other embodiments are within the scope of the following claims.

The invention claimed is:

1. A method comprising:
   transmitting a universal serial bus (USB) token packet to a first module within a medical device via an internal bus within the medical device;
   when the fast module has a data packet to transfer, receiving the data packet from the first module via the internal bus; and
   transferring the data packet to a second module within the medical device via the internal bus using a USB protocol.

2. The method of claim 1, further comprising encoding the data packet using a non return to zero inverted (NRZI) encoding scheme.

3. The method of claim 1, further comprising transferring the data packet in one of an isoebronous mode, an interrupt mode, a bulk data transfer mode, or a control mode.

4. The method of claim 1, further comprising, when the first module has no data packet to transfer, receiving an indication that the first module has no data packet to transfer.

5. The method of claim 1, further comprising assigning an address to each of the first and second modules.

6. The method of claim 1, further comprising associating at least one pipe with each of the first and second modules.

7. The method of claim 1, wherein the medical device comprises at least one of a therapy control module, a user interface module, or a patient parameters module.

8. The method of claim 1, wherein the medical device comprises a defibrillator.

9. A processor-readable medium containing instructions for causing a processor in a medical device to:
   transmit a universal serial bus (USB) token packet to a first module within the medical device via an internal bus within the medical device;
   when the first module has a data packet to transfer, receive the data packet from the first module via the internal bus; and
   transfer the data packet to a second module within the medical device via the internal bus using a USB protocol.

10. The processor-readable medium of claim 9, further containing processor-executable instructions for encoding the data packet using a non return to zero inverted (NRZI) encoding scheme.

11. The processor-readable medium of claim 9, further containing processor-executable instructions for transferring the data packet in one of an isoebronous mode, an interrupt mode, a bulk data transfer mode, or a control mode.

12. The processor-readable medium of claim 9, further containing processor-executable instructions for, when the first module has no data packet to transfer, receiving an indication that the first module has no data packet to transfer.

13. The processor-readable medium of claim 9, further containing processor-executable instructions for assigning an address to each of the first and second modules.

14. The processor-readable medium of claim 9, further containing processor-executable instructions for associating at least one pipe with each of the first and second modules.

15. The processor-readable medium of claim 9, wherein the medical device comprises at least one of a therapy control module, a user interface module, or a patient parameters module.

16. The processor-readable medium of claim 9, wherein the medical device comprises a defibrillator.

17. A medical device comprising:
   a control module within the medical device;
   a plurality of functional modules within the medical device; and
   an internal bus within the medical device coupled to the control module and to the plurality of functional modules, the internal bus arranged to transfer data packets between the control module and the functional modules according to a universal serial bus (USB) protocol.

18. The medical device of claim 17, wherein the plurality of functional modules comprises a therapy control module.

19. The medical device of claim 18, wherein the therapy control module controls delivery of an electric shock to a patient via a defibrillator electrode.

20. The medical device of claim 17, wherein the plurality of functional modules comprises a user interface module.

21. The medical device of claim 20, wherein the user interface module is communicatively coupled to at least one of a keyboard, a display screen, a strip chart recorder, an LED arrangement, a rotary encoder device, or a touch screen.

22. The medical device of claim 17, wherein the plurality of functional modules comprises a patient parameters module.

23. The medical device of claim 22, wherein the patient parameters module is configured to obtain at least one of multi-lead electrocardiogram (ECG) measurements, electroencephalogram (EEG) measurements, vital sign measurements, non-invasive blood pressure (NIBP) measurements, invasive blood pressure measurements, temperature measurements, end-tidal carbon dioxide ($ETCO_2$) information, or pulse oximetry ($SpO_2$) information from a patient.

24. The medical device of claim 17, wherein the plurality of functional modules comprises an expansion module to communicate data with at least one device external to the medical device.

25. The medical device of claim 24, wherein the expansion module is selected from the group consisting of: USB-compatible root hub, a hub, a simple device, and a complex device.

26. The medical device of claim 17, wherein the data packets are encoded using a non return to zero inverted (NRZI) encoding scheme.

27. The medical device of claim 17, wherein the data packets are transferred in at least one of an isochronous mode, au interrupt mode, a bulk data transfer mode, or a control mode.

28. The medical device of claim 17, wherein the control module is configured to assign addresses to the functional modules.

29. The medical device of claim 17, wherein the control module is configured to associate pipes with the functional modules.

30. The medical device of claim 17, wherein the medical device comprises a defibrillator.

31. An external defibrillator comprising:
a medical device enclosure;
an internal control module within the medical device enclosure;
a plurality of internal functional modules within the medical device enclosure, wherein the functional modules include at least a therapy control module that controls delivery of an electric shock to a patient via a defibrillator electrode, and a patient parameters module tat collects physiological parameter information from the patient; and
an internal bus within the medical device enclosure coupled to the control module and to the plurality of functional modules, the internal bus arranged to transfer data packets between the control module and the functional modules according to a universal serial bus (USB) protocol.

32. The external defibrillator of claim 31, wherein the patient parameters module is configured to obtain at least one of an electrocardiogram (ECG), non-invasive blood pressure (NIBP) measurements, end-tidal carbon dioxide ($ETCO_2$) information, or pulse oximetry ($SpO_2$) information from a patient.

33. The external defibrillator of claim 31,
wherein the plurality of functional modules comprises an expansion module, and
wherein the control module within the medical device enclosure communicates with an external device outside of the medical device enclosure via the internal bus within medical device enclosure and the expansion module.

34. The external defibrillator of claim 33, wherein the expansion module comprises a USB-compatible hub.

* * * * *

UNITED STATES PATENT AND TRADEMARK OFFICE
CERTIFICATE OF CORRECTION

PATENT NO. : 7,162,306 B2
APPLICATION NO. : 09/992708
DATED : January 9, 2007
INVENTOR(S) : Glen D. Caby et al.

It is certified that error appears in the above-identified patent and that said Letters Patent is hereby corrected as shown below:

In column 7, line 49, in Claim 1, delete "fast" and insert -- first --, therefor.

In column 7, line 59, in Claim 3, delete "isoebronous" and insert -- isochronous --, therefor.

In column 8, line 23, in Claim 11, delete "isoebronous" and insert -- isochronous --, therefor.

In column 9, line 12, in Claim 25, before "USB-compatible" insert -- a --.

In column 9, line 19, in Claim 27, delete "au" and insert -- an --, therefor.

In column 10, line 6, in Claim 31, delete "tat" and insert -- that --, therefor.

Signed and Sealed this

Eighth Day of December, 2009

David J. Kappos
*Director of the United States Patent and Trademark Office*